(12) United States Patent
Mark et al.

(10) Patent No.: US 10,687,815 B2
(45) Date of Patent: Jun. 23, 2020

(54) CLIP FOR A MEDICAL IMPLANT

(71) Applicant: Medtentia International Ltd Oy, Espoo (FI)

(72) Inventors: Pugh Mark, Coolaney (IE); Ger O'Carroll, Castlebaldwin (IE); Adrian Moran, Ballinfull (IE)

(*) Notice: Subject to any disclaimer, the term of this patent is extended or adjusted under 35 U.S.C. 154(b) by 332 days.

(21) Appl. No.: 15/323,422

(22) PCT Filed: Jul. 2, 2015

(86) PCT No.: PCT/EP2015/065149
§ 371 (c)(1),
(2) Date: Jan. 1, 2017

(87) PCT Pub. No.: WO2016/001382
PCT Pub. Date: Jan. 7, 2016

(65) Prior Publication Data
US 2017/0156731 A1    Jun. 8, 2017

Related U.S. Application Data

(60) Provisional application No. 62/019,935, filed on Jul. 2, 2014.

(51) Int. Cl.
*A61F 2/24* (2006.01)
*A61B 17/08* (2006.01)
*A61B 17/128* (2006.01)
*A61B 17/122* (2006.01)
(Continued)

(52) U.S. Cl.
CPC ............ *A61B 17/083* (2013.01); *A61B 17/10* (2013.01); *A61B 17/122* (2013.01); *A61B 17/128* (2013.01); *A61B 17/1285* (2013.01); *A61B 17/12122* (2013.01); *A61F 2/2466* (2013.01); *A61F 2/2445* (2013.01)

(58) Field of Classification Search
CPC . A61B 17/083; A61B 17/10; A61B 17/12122; A61B 17/128; A61B 17/1285; A61F 2/2442; A61F 2/2445; A61F 2/2466
See application file for complete search history.

(56) References Cited

U.S. PATENT DOCUMENTS

| 5,797,931 A | 8/1998 | Bito |
| 6,610,073 B1 | 8/2003 | Levinson |
| 2004/0176784 A1 | 9/2004 | Odada |

(Continued)

FOREIGN PATENT DOCUMENTS

| DE | 102011001705 A1 | 10/2012 |
| EP | 1810622 A1 | 7/2007 |

(Continued)

*Primary Examiner* — Sarah A Simpson
(74) *Attorney, Agent, or Firm* — Patent Grove LLC; Tomas Friend

(57) ABSTRACT

A clip having a delivery shape and an implanted shape has a first and a second leg joined at their distal ends at a distal point of the clip. The distal point forms a tapered shape of the clip and is adapted to pierce tissue. Proximal ends of the first and second legs are spaced apart in the delivery shape by a first distance. The proximal ends are compressible to the implanted shape in which the legs are spaced apart by a second distance that is shorter than the first distance. A related delivery device, a related system, and a delivery method are also disclosed.

19 Claims, 12 Drawing Sheets

(51) Int. Cl.
*A61B 17/10* (2006.01)
*A61B 17/12* (2006.01)

(56) References Cited

U.S. PATENT DOCUMENTS

| | | |
|---|---|---|
| 2005/0080454 A1 | 4/2005 | Drews |
| 2008/0033457 A1 | 2/2008 | Francischelli |
| 2008/0188872 A1 | 8/2008 | Duff |
| 2008/0208330 A1* | 8/2008 | Keranen ............... A61F 2/2448 623/2.36 |
| 2009/0125038 A1 | 5/2009 | Ewers |
| 2014/0039524 A1 | 2/2014 | Schulz et al. |
| 2014/0309730 A1* | 10/2014 | Alon .................... A61F 2/2409 623/2.11 |
| 2016/0120645 A1* | 5/2016 | Alon .................... A61F 2/2442 623/2.4 |

FOREIGN PATENT DOCUMENTS

| | | |
|---|---|---|
| WO | 2006098994 A1 | 9/2006 |
| WO | 2012126477 A1 | 9/2012 |

\* cited by examiner

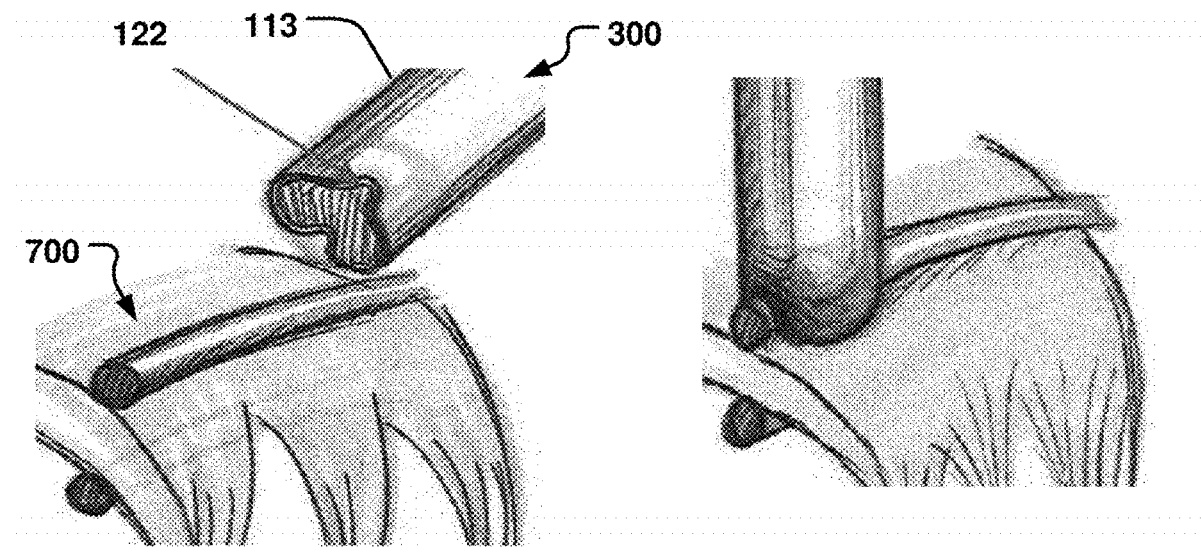
Fig. 2a
Fig. 2b
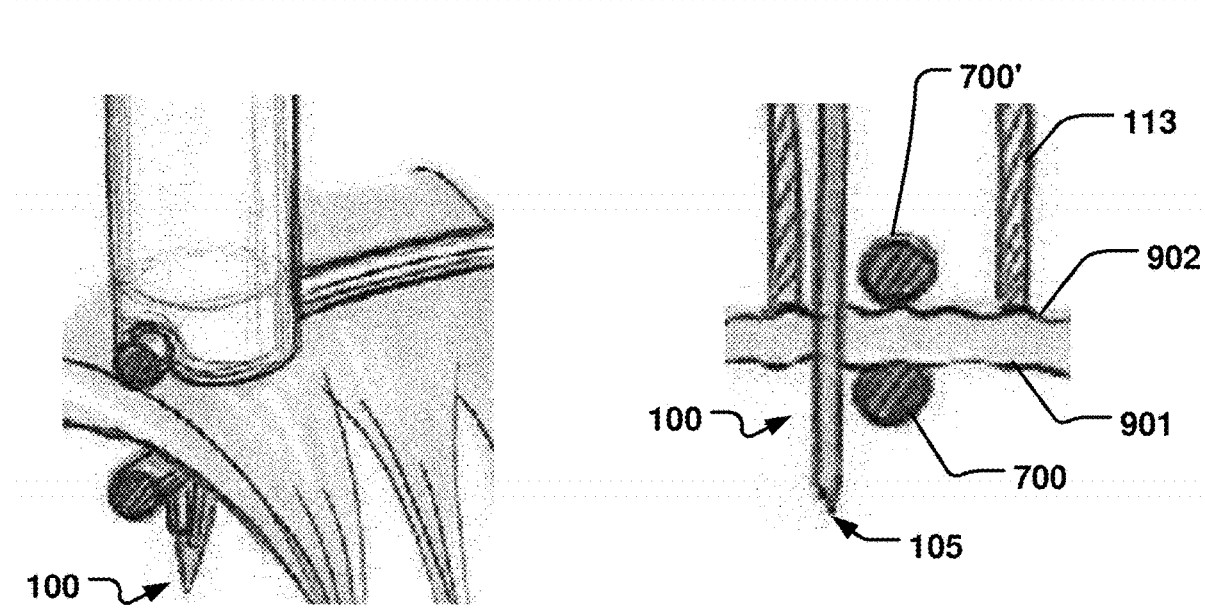
Fig. 2c
Fig. 2d

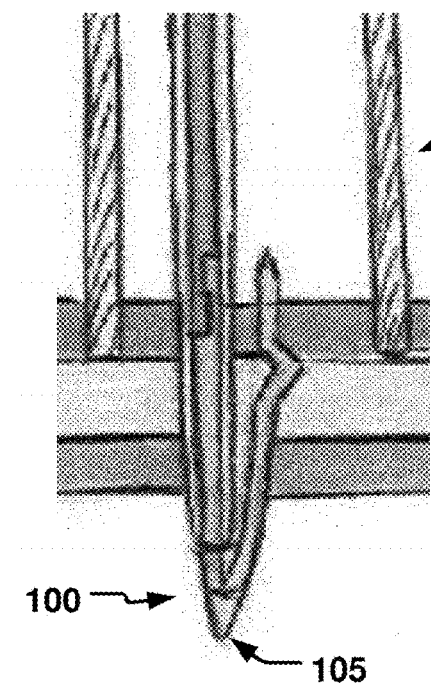
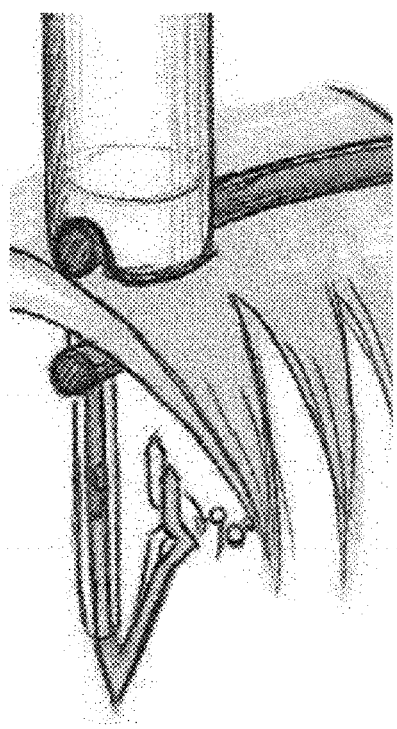
Fig. 2e    Fig. 2f
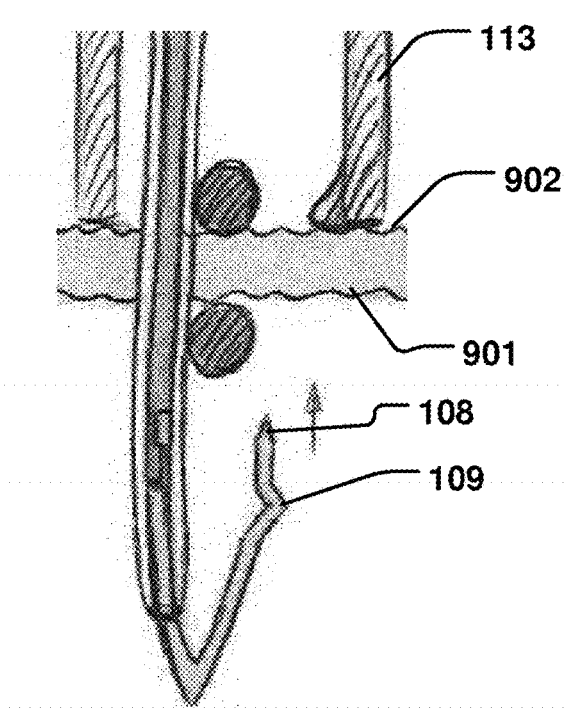
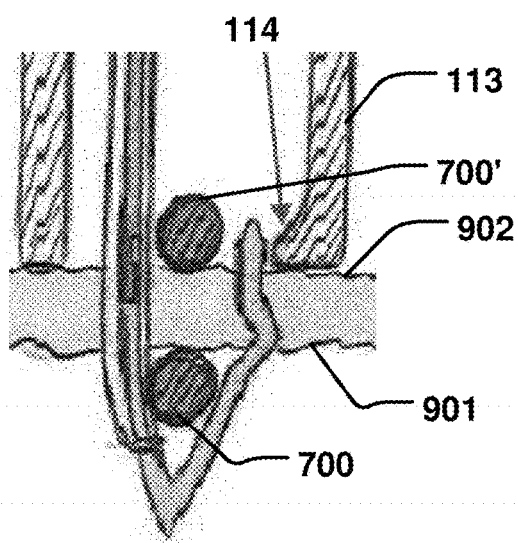
Fig. 2g    Fig. 2h

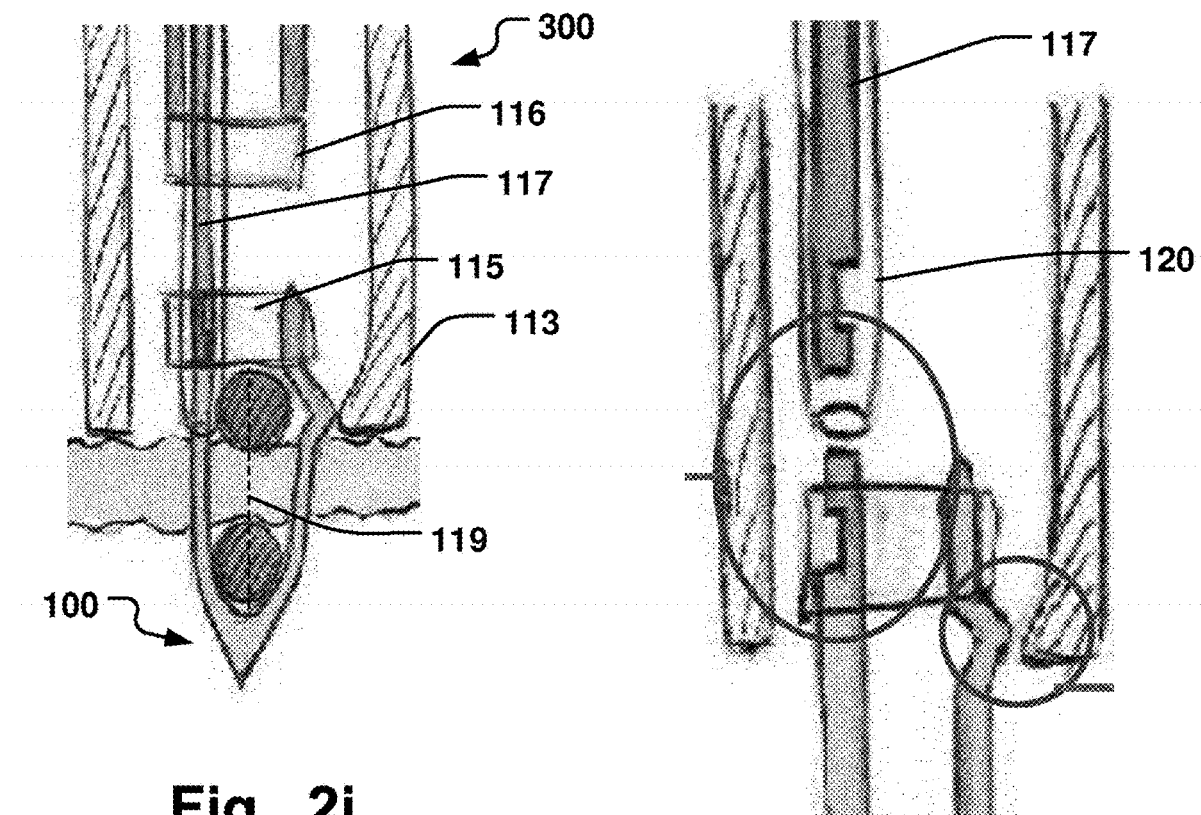
Fig. 2i
Fig. 2j
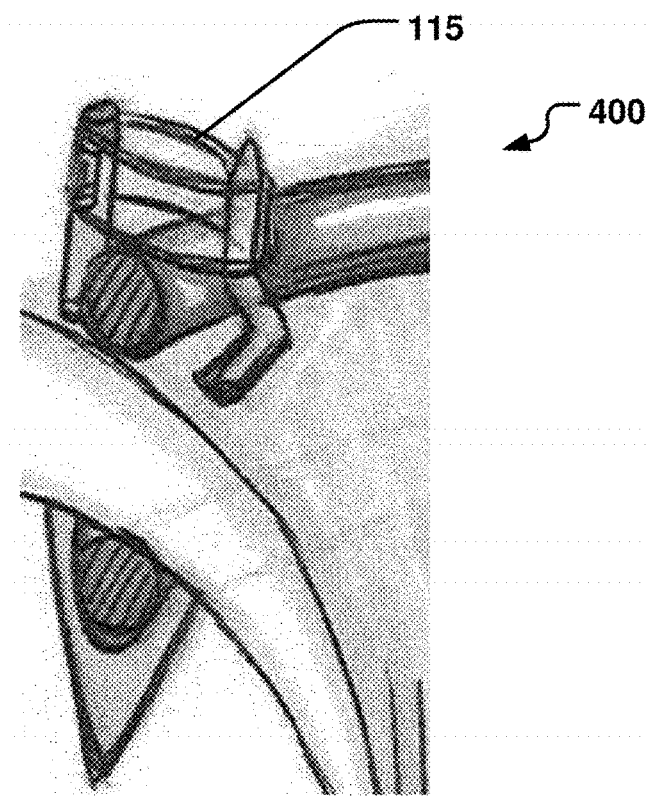
Fig. 2k

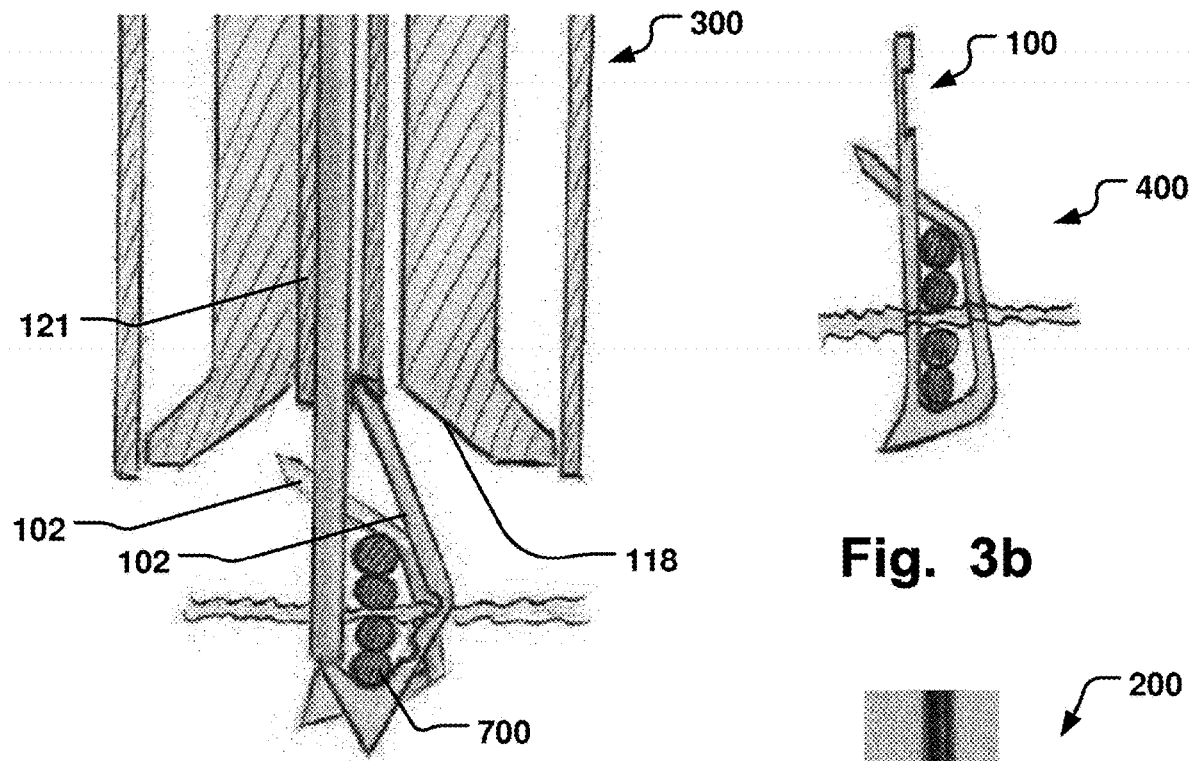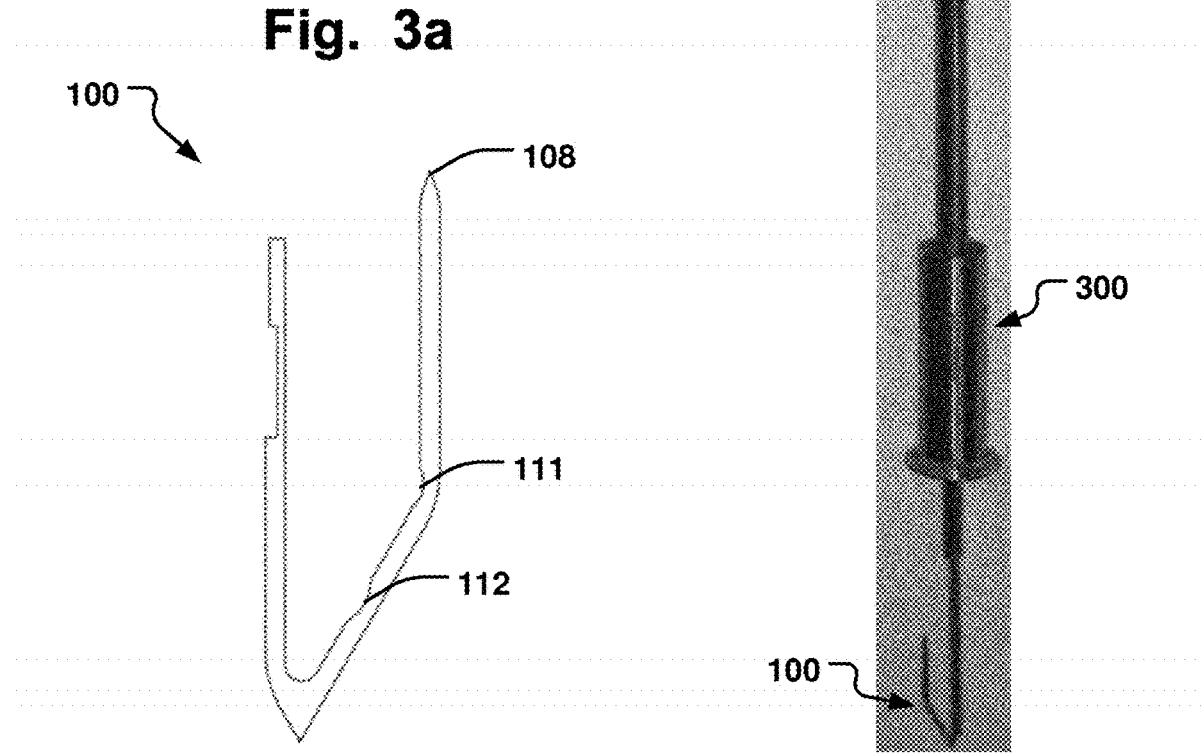

CLIP FOR A MEDICAL IMPLANT

FIELD OF THE INVENTION

This invention pertains in general to the field of clips being attachable to tissue. More particularly the invention relates to clips for fixating annuloplasty implants to heart valve tissue, a method therefore, and clip delivery device.

BACKGROUND OF THE INVENTION

Diseased mitral valves frequently need repair to function properly. The mitral valve leaflets or supporting chordae may degenerate and weaken or the annulus may dilate leading to valve leak (valve insufficiency). Mitral valve repair is frequently performed with aid of an annuloplasty ring or helix, used to reduce the diameter of the annulus, or modify the geometry of the annulus in any other way. In some procedures the annuloplasty ring is fixated around the annulus of the valve.

U.S. Pat. No. 8,603,161 discloses a device for attaching a prosthesis, having a slide that is pushed against a substantially horizontal anvil to cause legs of a clip to rotate outwards. The anvil can be slid out of the way so that the clip is released from the device.

A problem with the prior art is the complexity of the devices which requires a several operating steps in which the several movable parts must be engaged in sequence. The procedure thus becomes more complicated and time consuming. Complex devices that are expensive to manufacture also lead to loosing the advantage of using disposable single use devices. A further problem with prior art clips is limited possibilities to manipulate the clip once it has been attached to tissue. It is important to be able to attach the clip at the desired site with high accuracy, which can be compromised if the clip can not be sufficiently manipulated throughout the procedure until it has been fixated into the final position. Frequently the target site may be of complex anatomy and there may be movement, such as the motion of the beating heart in addition to the operator's movements, that lead to difficulties in positioning a clip when having such lack of manipulation abilities.

Further, devices and clips in the prior art are not suitable for annuloplasty implants such as helix rings that are to be positioned on either side of a heart valve. Such device would not provide sufficient fixation of such implant and lead to traumatic effects since the fixation structure must ensure the correct position of the device over time.

The above problems may have dire consequences for the patient and the health care system. Patient risk is increased.

Hence, an improved clip for attaching annuloplasty implants such as helix rings would be advantageous and in particular allowing for ensuring long-term functioning, less complex procedure, and increased patient safety. A delivery device for providing such improvements, and a related method would also be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention a clip is provided having a delivery shape and an implanted shape, and comprising a first and a second leg being joined at respective distal ends, at a distal point of the clip. The distal point forms a tapered shape of the clip and is adapted to pierce tissue. The proximal ends of the first and second legs are spaced apart in the delivery shape by a first distanc. The proximal ends are compressible to the implanted shape in which the legs are spaced apart by a second distance which is shorter than the first distance.

According to a second aspect of the invention a system is provided comprising a clip according to the first aspect of the invention and a delivery device having a connector wire being releasably connectable to the first or second leg of the clip.

According to a third aspect of the invention a system is provided comprising a clip according to the first aspect of the invention and an annuloplasty implant, such as an annuloplasty ring. The first and second legs of the clip form an upward open receiving portion, extending from the distal point, the receiving portion being adapted to receive and fixate the position of the implant to a heart valve.

According to a fourth aspect of the invention a method of delivering a clip according to the first aspect of the invention to a target site is provided. The method comprises penetrating tissue of a proximal side of a heart valve with the distal point so that the entire first or second leg is pushed through the tissue to an opposite side of said heart valve, withdrawing the clip towards the opposite side so that an annuloplasty implant is captured between the first and second leg, fixating the annuloplasty ring to the heart valve by locking the position of the clip.

According to a fifth aspect of the invention a clip for use in a stapling device is disclosed, the clip having a delivery shape and a relaxed shape and comprises legs extending at least partly and substantially parallel to a longitudinal direction of said clip, each of the legs having a proximal portion curved in an inward direction to form a bridging portion joining the proximal portions of the legs, and each of legs having a distal portion, wherein in said relaxed shape, each of the distal portions being curved in an outward direction, substantially opposite said inward direction.

According to a further aspect of the invention a method of delivering a clip according to the fifth aspect of the invention to a target site is disclosed, comprising positioning a proximal portion of said clip over an annuloplasty ring at a first side of a heart valve, positioning a distal portion of said clip having a tip on a second side of said heart valve, opposite said first side, so that said tip portion is arranged to penetrate tissue on said second side.

Further embodiments of the invention are defined in the dependent claims, wherein features for the second and subsequent aspects of the invention are as for the first aspect mutatis mutandis.

Some embodiments of the invention provide for securing long-term functioning and position of an annuloplasty implant.

Some embodiments of the invention provide for less complex fixation procedures of an annuloplasty implant.

Some embodiments of the invention provide for a reduced risk of damaging the anatomy such as the CS.

Some embodiments of the invention provide for secure fixation of annuloplasty implants while ensuring an atraumatic procedure.

Some embodiments of the invention provide for secure fixation of an annuloplasty implant on either side of a heart valve.

Some embodiments of the invention provide for increased accuracy when attaching a clip to a beating heart.

Some embodiments of the invention provide for a more secure attachment with a clip and improved fixation of annuloplasty rings having different diameters.

Some embodiments of the invention provide for reducing the risk of damaging tissue with a clip.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 2a-k are illustrations of a clip and a delivery device according to the invention, and of a method of delivering the clip at a target site, according to embodiments of the invention;

FIGS. 3a-b are illustrations of a clip and a delivery device according to the invention, and of a method of delivering the clip at a target site, according to embodiments of the invention;

FIG. 4 is an illustration of a clip according to embodiments of the invention;

FIG. 5 is an illustration of a clip and a delivery device according to embodiments of the invention;

FIG. 9b is a top-down view of the illustration in FIG. 9a;

DESCRIPTION OF EMBODIMENTS

Figures 1A, 1B:
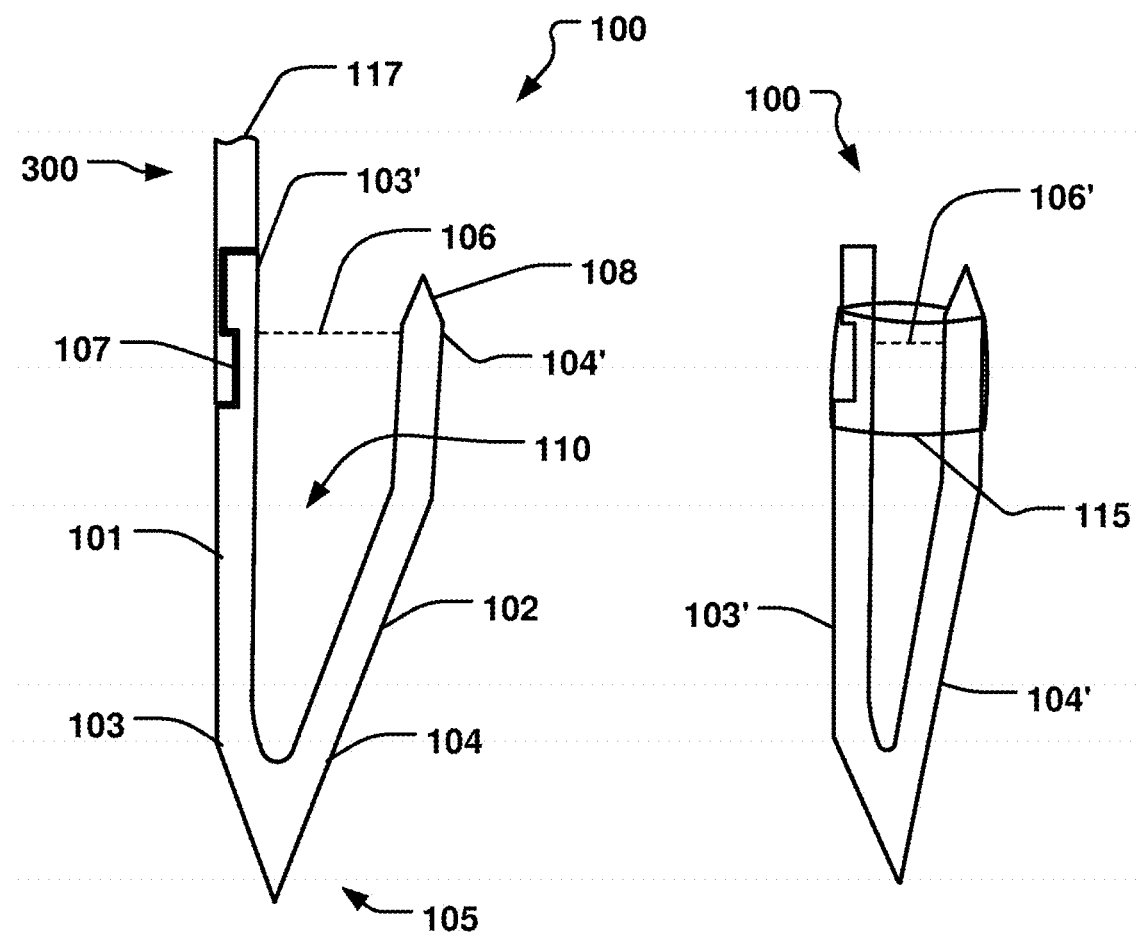
FIGS. 1a-b are illustrations of a clip according to embodiments of the invention.
Figure 6:
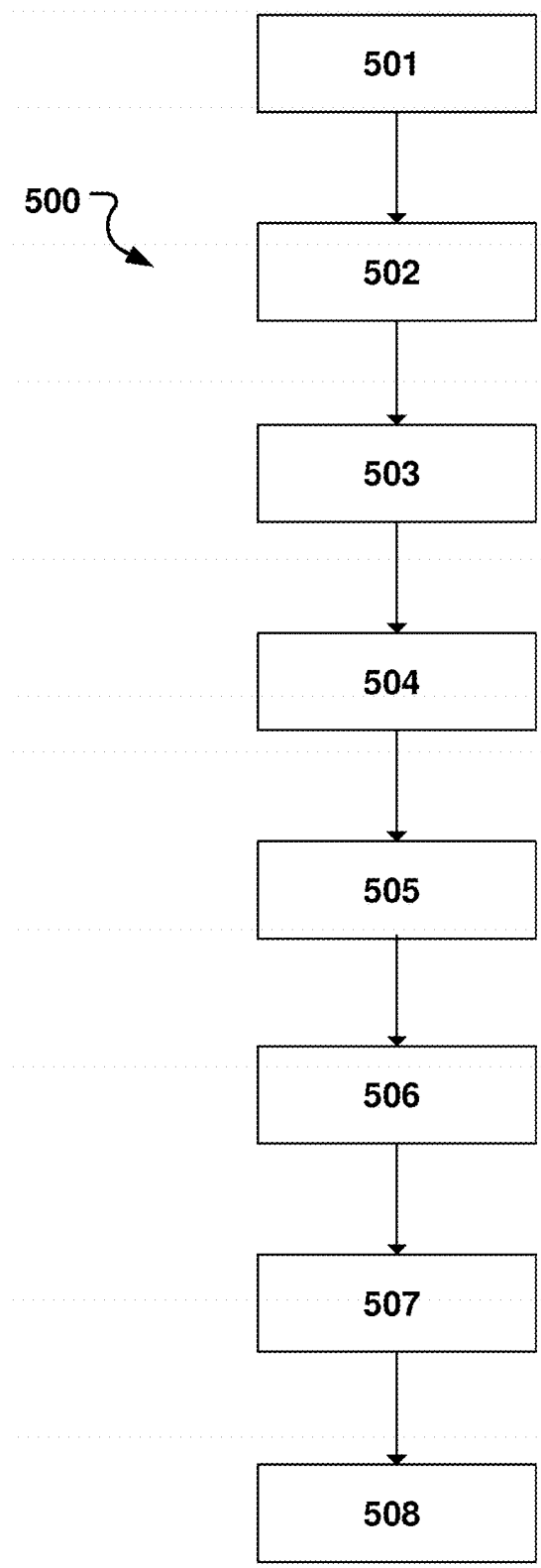
FIG. 6 is a flow chart illustrating a method according to embodiments of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable to fixation of annuloplasty implants to valve tissue. However, it will be appreciated that the invention is not limited to this application but may be applied to many other procedures involving attachment of clips to tissue, including for example fixation of other medical implantable devices or stapling parts of tissue together, in any medical procedure.

FIG. 1 illustrates a clip 100 having a delivery shape (FIG. 1a) and an implanted shape (FIG. 1b) comprising a first and a second leg 101, 102, being joined at respective distal ends 103, 104, at a distal point 105 of the clip 100. The distal point 105 forms a tapered shape of the clip and is adapted to pierce tissue. The proximal ends 103', 104', of the first and second legs are spaced apart in the delivery shape by a first distance 106. The proximal ends 103', 104', are compressible to the implanted shape in which the legs are spaced apart by a second distance 106' which is shorter than the first distance 106. Having a tapered distal point 105 opposite the proximal ends 103', 104', of the legs allows for reversed insertion of the clip compared to prior art clips that must be inserted with the free ends of the legs first. This thereby allows for manipulation of free ends of legs, i.e. the proximal ends 103', 104', from the side of the operator, which may facilitate the fastening of the clip 100. It is thus possible, for example, to capture an implant 700, 700', as illustrated in FIGS. 2a-k and 3a-b between the legs 101, 102, and thereafter manipulate the proximal ends 103', 104', of the legs for fixation of the implant. This also allows for fixation of a portion of an implant 700 on the backside or reversed side 901 of a wall of tissue with respect to the operator who faces the proximal side, such as the opposite side 901 of a heart valve, as illustrated e.g. in FIG. 2h. The clip 100 thus allows for a convenient procedure of fastening implants on the reversed side of such anatomies. The method illustrated in FIGS. 2a-k will be described in more detail below. Further, since the proximal ends 103', 104', of the legs can be manipulated and compressed it is possible to apply a force to the implant 700, 700', in order to provide a secure fixation thereof. The legs 101, 102, can also be compressed towards each other in the implanted state, such that the implant 700, 700', is unable to move out of the clip, i.e. the distance 106' is smaller than the relevant cross-sectional dimension of the implant, without having the clip 100 to exert a force towards the implant 700, 700'. FIGS. 3a-b illustrates bending of the legs 101, 102, so that the implant 700 is trapped in the clip 100. In this case, the amount of bending of the legs 101, 102, may vary, and as mentioned, the clip may or may not apply a force into the implant 700.

As illustrated in FIG. 1b, a fixation member 115 may also be attached to the clip 100, being further described below. This allows for securing the clip an a desired shape after implantation, i.e. the implanted shape, that allows for trapping the implant 700. It is also conceivable that the fixation member 115 alone is sufficient to provide the necessary fixation of the implant 700 and that the legs do not need to be significantly compressed towards each other to trap the implant 700. The fixation member 115 may be an annular structure that loops the proximal ends 103', 104', of the legs or it may be an elongated connecting structure such as a suture.

In case the material of the clip 100 allows for manipulation of the shape of the clip into the desired shape in the implanted state, the fixation member 115 could be omitted. For example, the material of the clip 100 may be a shape memory material that is set in a heat set shape where the relaxed state of the clip is the implanted shape, having a reduced length 106' for trapping the implant 700. A restraining force could then be applied to force the legs 101, 102, into the spaced-apart configuration 106, when capturing the implant 700, and thereafter removing the restraining force to allow the clip to assume the compressed implanted shape 106'. Alternatively, the clip 100 has a heat set shape where the relaxed unstrained state is the delivery shape having the expanded length 106 between the legs 101, 102. At least one of the legs 101, 102, is then bent by applying a force after having trapped the implant, as discussed in relation to FIGS. 3a-b.

The distal point 105 of the clip 100 and at least a portion of (one of) the legs 101, 102, may form the tapered shape of the clip 100. This allows for a facilitated insertion of the clip 100 into the tissue since a larger portion of the total length of the clip may be tapered. At the same time, a compact clip dimension can be maintained.

The first 101 or second 102 leg may comprise a proximal connecting element 107 that is adapted to connect to a delivery device 300, as illustrated in FIG. 1a. This allows for a low-profile compact solution enabling easy access to the target site while having a secure connection to the delivery device 300. The connecting element 107 may comprise a recess or a protrusion, or a combination of both, that interlocks with a corresponding mating surface of the delivery device 300. FIG. 2j illustrates an example where the delivery device 300 comprises a connector wire 117 having such mating surface and a sheath 120 that is reversibly positionable over the interlocking connection for securing the surfaces together, see e.g. FIG. 2j. Thus, withdrawal of the sheath 120 releases the clip 100 from the connector wire 117. Other releasable connection elements are conceivable, such as suture-, screw-, or clamp connections.

The clip 100 may comprise a proximal tapered portion 108 that is adapted to pierce tissue, as illustrated in e.g. FIG. 1a and FIG. 2g. This allows for easy penetration of the tissue of the opposite side 901 of e.g. a heart valve, which is not visible to the operator, as the clip is withdrawn, i.e. pulled, towards the operator. The proximal tapered portion 108 is thus tapered in a direction substantially opposite to the direction of taper of the tapered shape of the distal point 105 of the clip. This accordingly facilitates fixation of an implant 700 to the aforementioned oppositely oriented tissue wall 901, see e.g. further FIG. 2h.

The clip 100 may be substantially V-shaped. This further improved the tissue piercing ability of the clip 100, since the clip 100 may be overall tapered in shape, while having a compact length since an implant 700, 700', may be trapped in the V-shaped structure. It is also possible that the clip 100 can have other shapes, such as U-shaped. The apex point of the U-shape, i.e. the bridging portion between legs 101, 102, may thus have a distal portion that is adapted to pierce tissue.

The first and second legs 101, 102, may form an upward open receiving portion 110, extending from the distal point 105 (e.g. FIG. 1a). The receiving portion 110 may be adapted to receive and fixate the position of an implant 700, 700', such as an annuloplasty ring to a first side 901 of a heart valve. The receiving portion 110 may thus have a shape that allows for capturing the implant 700, 700'. For example, the receiving portion 110 may have a shape that is dimensioned to receive an implant of desired size. The receiving portion 110 may also partially conform to the cross-section of the implant. In the latter case, a slightly upwardly concave shape may provide a more secure hold to an implant having an circular or oval cross-sectional shape, such as an annuloplasty ring.

The first or second 101, 102, leg may comprises at least one reduced diameter portion 111, 112, as illustrated in FIG. 4. The reduced diameter portion 11, 112, is a predefined bending point at which the clip 100 bends upon application of a force when, in use, the clip 100 is being transformed from the delivery shape to the implanted shape. This can accordingly facilitate fixation of the clip around an implant 700, 700'. FIG. 3a illustrates application of a force towards the second leg 102 of the clip 100, that results in bending of the clip at the reduced diameter portion 111, 112. FIG. 4 illustrates two reduced diameter portions, but it is also possible that one reduced diameter portion is sufficient.

A system 200 is disclosed (FIGS. 1a, 2c-k, 3a, 5) comprising a clip 100 as described above, having a first and a second leg 101, 102, being joined at respective distal ends 103, 104, at a distal point 105 of the clip, the distal point forming a tapered shape of the clip being adapted to pierce tissue, and a delivery device 300 having a connector wire 117 being releasably connectable to said first or second leg of said clip. The connector wire 117, which has been described above in relation to the clip 100, may be connected to the first or second leg 101, 102, having a connecting element 107.

The delivery device 300 may comprises a catheter 113, as seen in e.g. FIG. 2g. The first or second leg 103, 104, may comprise a proximal engagement portion 109 extending radially outwardly towards, i.e. towards the catheter 113 when, in use, being withdrawn into the catheter 113. Thus when the engagement portion 109 is withdrawn into the catheter an edge portion 114 (FIG. 2h) of the catheter push the engagement portion radially inwards. Thus the proximal ends 103', 104', of legs are pushed towards each other, which may facilitate positioning of the fixation member 115 to the legs 101, 102. The force applied by the catheter towards the engagement portion 109 is removed when the catheter 113 is removed, so that a tensile force can be applied from the fixation member 115 towards the clip 100. The edge portion 114 may be provided as a protrusion on the edge of the catheter, extending radially inwards.

Thus, the system may comprise the fixation member 115, which can be attachable to the proximal ends 103', 104', of the first and second legs of the clip, and being adapted to fixate the clip 100 in the implanted shape.

The delivery device 300 may comprise a sheath 116 for attaching said fixation member 115 to the clip 100, as schematically illustrated in FIG. 2i. The sheath 116 may thus be arranged inside the outer catheter 113. The delivery device 300 may further comprise the connector wire 117 that is engageable with the proximal connecting element 107 of the clip 100 for releasably connecting thereto. The sheath may surround the delivery wire 117.

The delivery device 300 may comprises an angled surface 118 that is engageable with the clip 100 for applying a force to bend a proximal end 103', 104', of first or second leg 101, 102, when, in use, being withdrawn towards the angled surface 118. The angled surface 118 is illustrated in FIG. 3a. A further catheter element 121, arranged radially inside the angled surface 118, may be provided to further compress the first or second leg of the clip 100, as illustrated in FIG. 3a.

A system 400 is disclosed (e.g. FIGS. 2k, 3b) comprising a clip 100 as described above having a first and a second leg 101, 102 being joined at respective distal ends 103, 104, at a distal point 105 of the clip, the distal point forming a tapered shape of the clip being adapted to pierce tissue, and comprising an annuloplasty implant 700, 700', such as an annuloplasty ring. The first and second legs 101, 102, form an upward open receiving portion 110, extending from said distal point 105, as discussed previously. The receiving portion 110 is adapted to receive and fixate the position of the implant 700, 700' of the system 400 to a heart valve.

The implant of the system 400 may comprise a helix-shaped implant having a first 700 and a second 700' ring. The receiving portion may be adapted to receive and fixate the first and second rings 700, 700', on either side 901, 902, of a heart valve.

The receiving portion 110 may have a length 119 corresponding to at least the sum of the diameters of the cross-sections of the first 700 and a second 700' ring of the helix-shaped implant positioned on either side of the heart valve. This allows for a secure fixation of a helix-shaped implant since the clip 100 can trap and contain the full cross-section of the implant.

The system 400 may further comprise the fixation member 115 being attachable to proximal ends 103', 104' of the first and second legs of the clip 100. The fixation member 115 is adapted to fixate the clip in the implanted shape, which can be achieved by providing tension on the first and second legs from the fixation member 115 against the annuloplasty implant 700, 700'.

A method 500 (FIGS. 2*a-k*, 6) of delivering a clip 100 to a target site is disclosed. The clip 100 has been described above. The clip 100 has first and a second legs 101, 102, being joined at respective distal ends 103, 104, at a distal point 105 of the clip, the distal point forming a tapered shape of the clip being adapted to pierce tissue. The method 500 comprises penetrating 501 tissue of a proximal side 902 of a heart valve with the distal point 105, FIG. 2*c-d*, so that the entire first leg 101 or second leg 102 is pushed through the tissue to an opposite side 901 of the heart valve, as seen in FIG. 2*f*. FIGS. 2*d-e* are two different side-views of the clip 100 partially penetrated into the tissue. The method further comprises withdrawing 502 the clip 100 towards the opposite side 901 so that an annuloplasty implant 700 is captured between the first and second leg 101, 102, as illustrated in FIGS. 2*g-h*. The annuloplasty ring 700 is fixated 506 to the heart valve by locking the position of the clip 100, as exemplified in FIG. 2*i* or 3*a*. Further, before the clip is pushed into the proximal 902, the delivery device 300 is positioned at the target site, as illustrated in e.g. FIGS. 2*a-b*, in which example the implant is a helix-shaped ring. In this example, the catheter 113 of the delivery device 300 has a recess 122 that is positioned over the proximal ring 700'. Also, before the clip 100 is withdrawn, it is rotated as illustrated in FIG. 2*f* so that the legs 101, 102, are positioned over the implant 700.

Thus, locking the position of the clip 100 may comprise attaching 507 a fixation member 115 to proximal ends 103', 104', of the first and second legs 101, 102, at the proximal side 902 to fixate the position of the clip around the annuloplasty ring 700, 700'. This is illustrated in FIG. 2*i* where the fixation member 115 is delivered to the clip from the delivery device 300, before being detached (FIG. 2*j*). The clip 100 and the fixation member 115 thus holds the implant 700 securely, FIG. 2*k*.

Locking the position of the clip 100 may also comprise bending 508 the first and/or second legs to reduce the distance 106, 106', between proximal ends 103', 104', of the first and second legs 101, 102, to fixate the position of the clip around the annuloplasty ring, as illustrated in FIGS. 3*a-b*.

The method 500 may comprise penetrating 503 tissue at the opposite side 901 of the heart valve with a proximal tapered portion 108 of the clip upon withdrawing of the clip 100, as illustrated in FIGS. 2*g-h*.

Withdrawing the clip 100 may comprise capturing 504 a first ring 700 of a helix-shaped implant, being positioned on the opposite side 901 of the heart valve, with the distal ends 103, 104, of the first and second legs, FIG. 2*h*. Subsequently, as the clip 100 is withdrawn further, i.e. pulled towards the delivery device 300, a second ring 700' of the helix-shaped implant is captured 505 on the proximal side 902 of the heart valve, with proximal ends 103', 104', of the first and second legs, FIGS. 2*h-i*.

Figure 7:
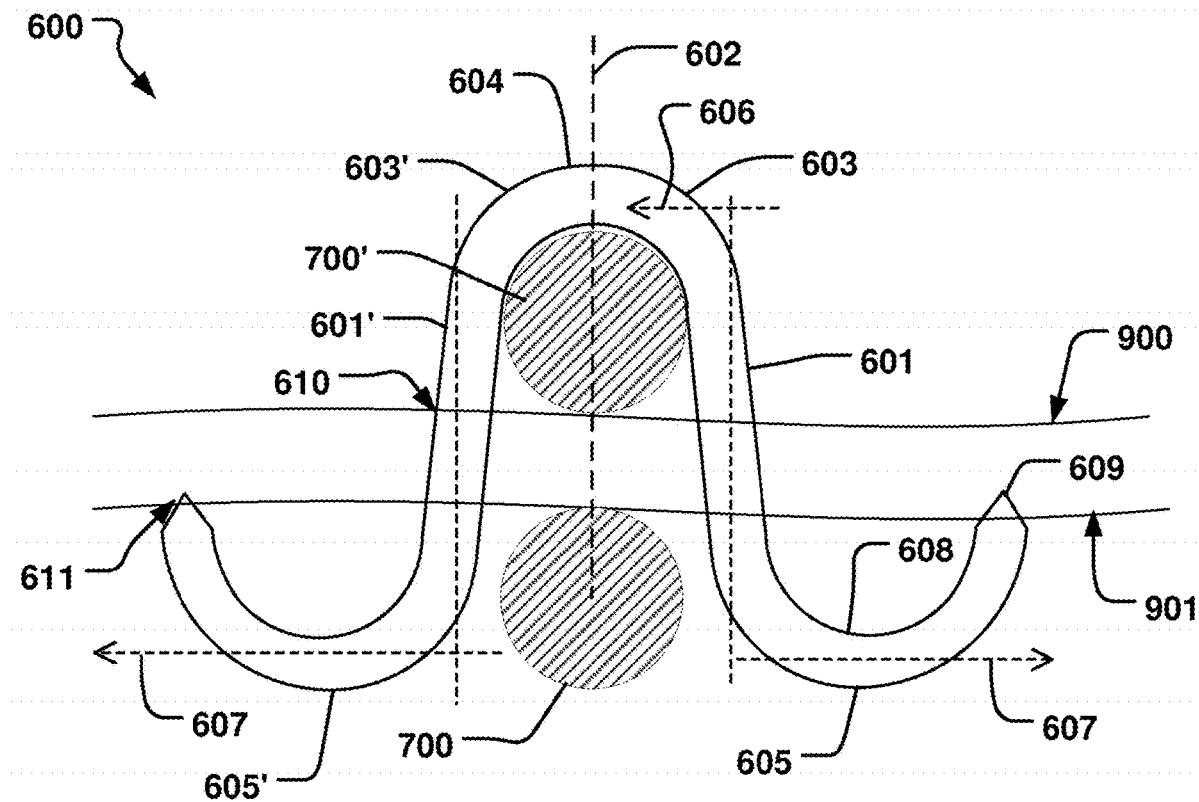
FIG. 7 is a side-view illustration of a clip according to another embodiment of the invention when fixating the position of an implant to tissue.
Figure 8:
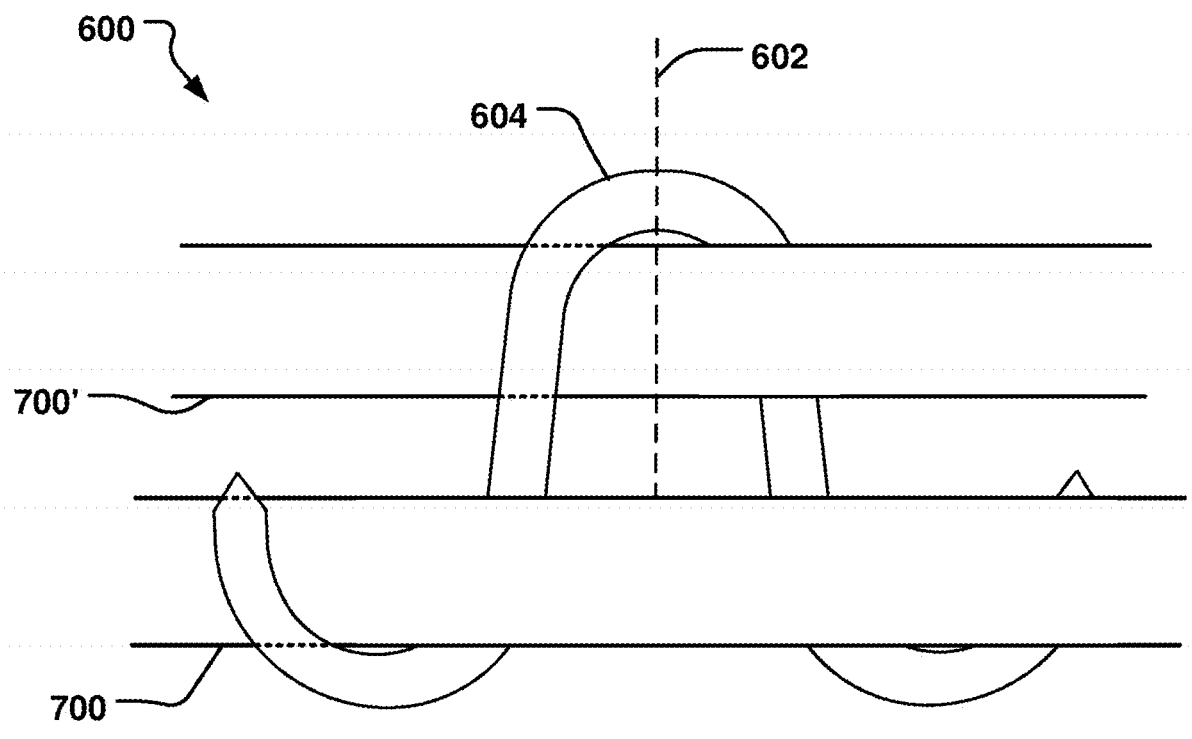
FIG. 8 is another illustration of a clip according to embodiments of the invention when fixating the position of an implant.
Figure 9A:
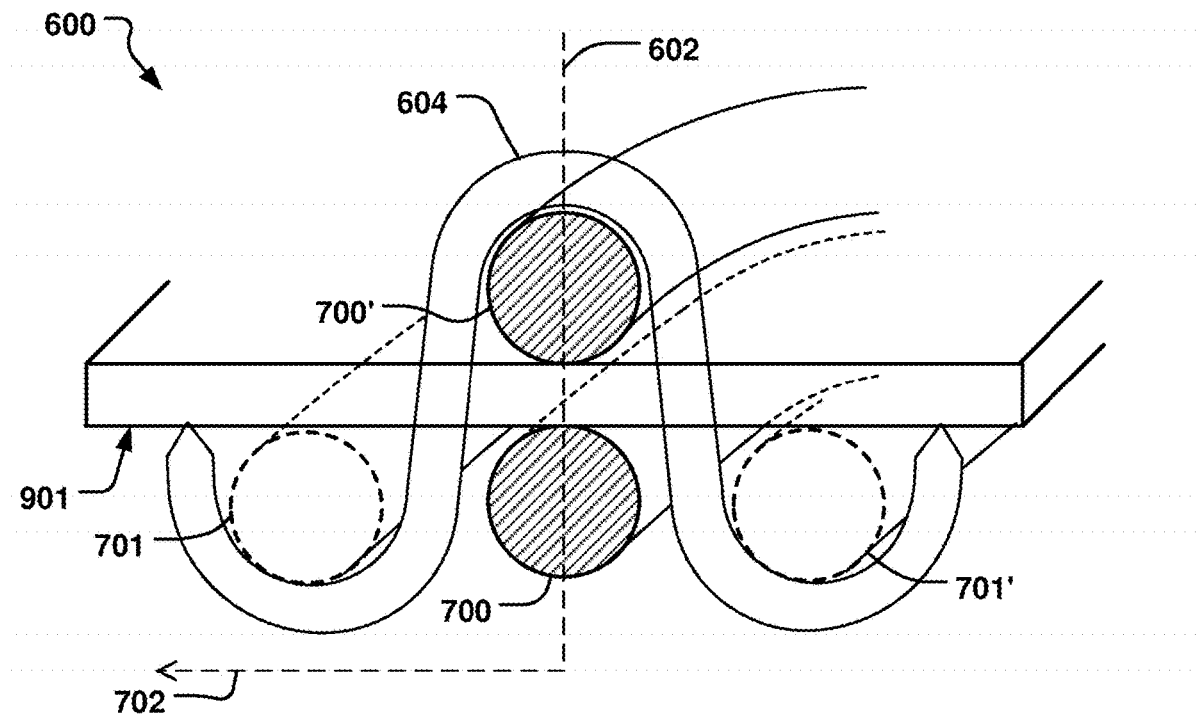
FIG. 9a is a perspective view illustration of a clip according to embodiments of the invention when fixating the position of an implant to tissue.
Figure 9B:
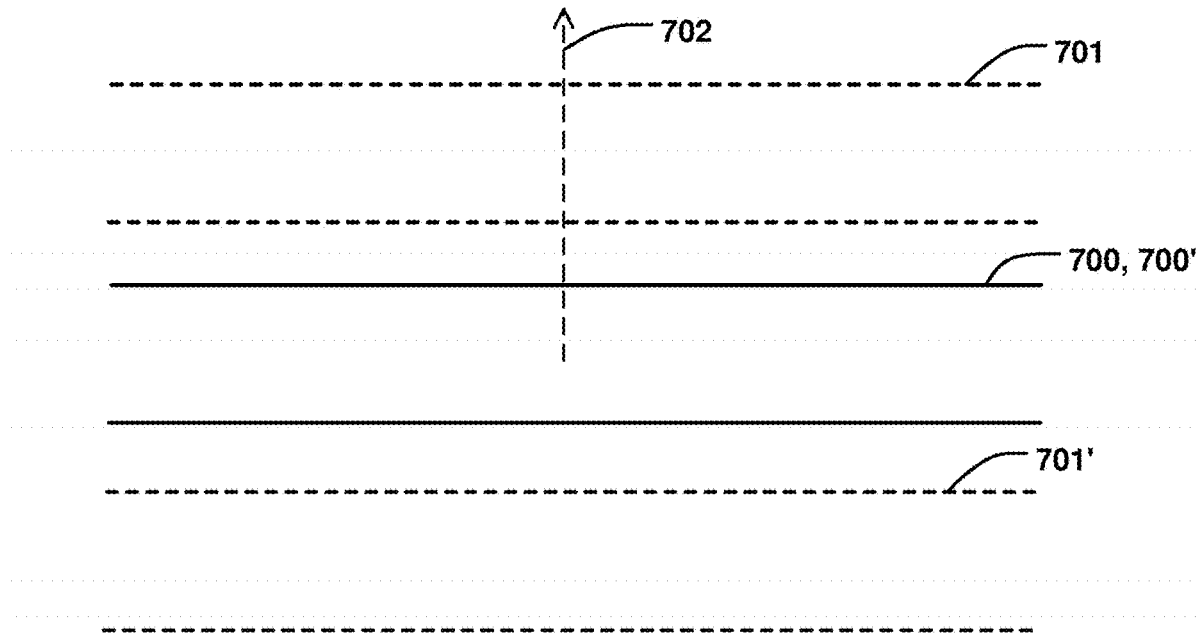
Figure 11:
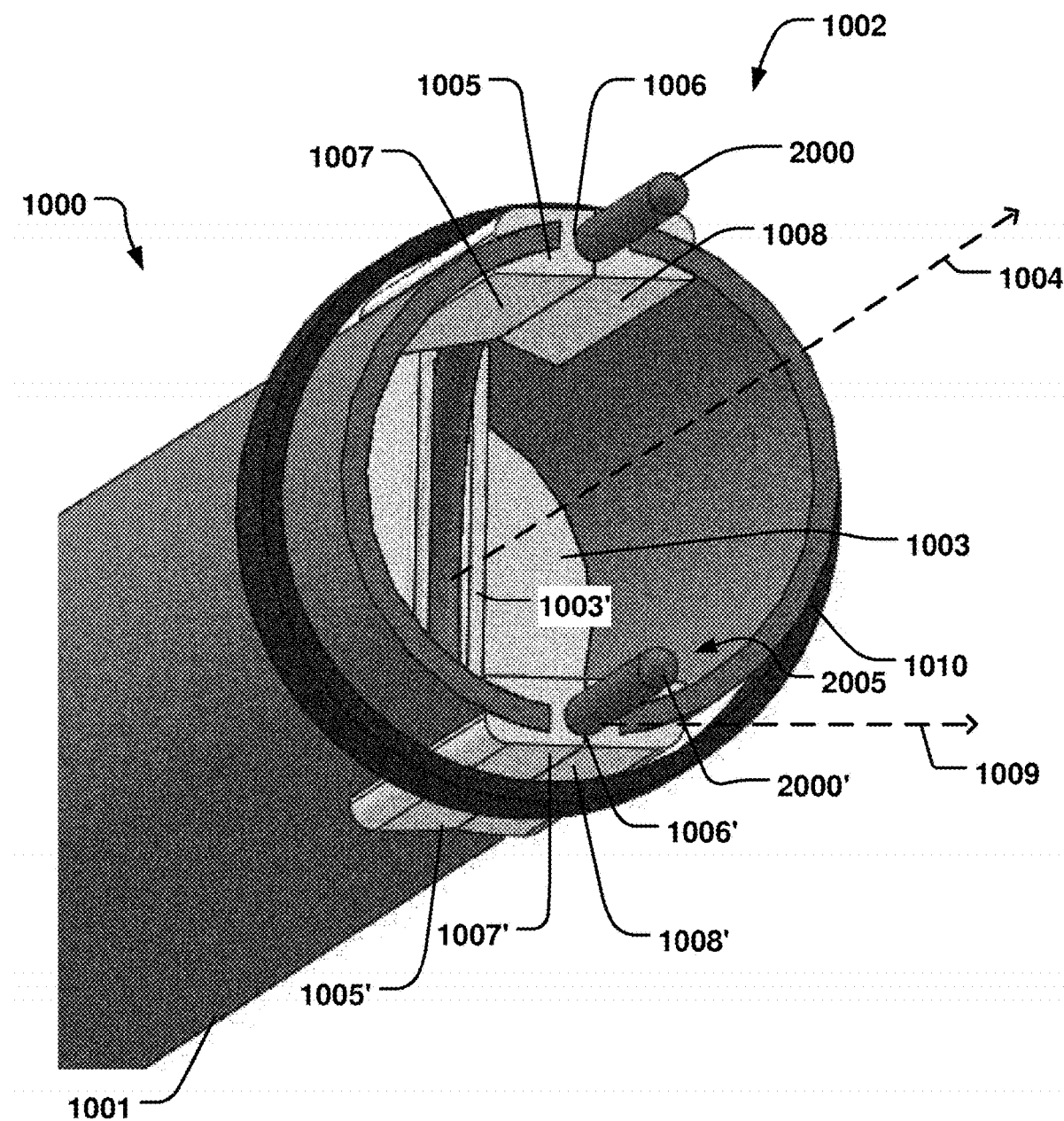
FIG. 11 is an illustration of a stapling device for delivering a clip according to FIGS. 7-9, 12, according to embodiments of the invention.

FIGS. 7-9 illustrates an alternative embodiment, showing a clip 600 for use in a stapling device, such as illustrated in FIG. 11, and described further below. The clip 600 has a delivery shape and a relaxed shape and comprises legs 601, 601', extending at least partly and substantially parallel to a longitudinal direction 602 of the clip. Each of the legs has a proximal portion 603, 603', curved in an inward direction 606 to form a bridging portion 604 joining the proximal portions of the legs, 603, 603'. Each of the legs has a distal portion 605, 605'. In the relaxed shape, each of the distal portions are curved in an outward direction 607, substantially opposite the inward direction 603. The outward curving of the distal portion 605, 605', is shown in FIG. 7, and also in FIGS. 8, 9*a*, 13. The distal portions thus create an increased retention of the clip towards the tissue wall 901, i.e. the wall opposite the direction of insertion of the clip. This also allows greater variation in the configuration of the implant, since the clip only grips the implant at one side of the tissue wall. The distal portions may however also grip the implant on the other side of the tissue wall, as illustrated in FIGS. 9*a-b*. In all, the outward curving of the distal portions allows for greater flexibility when attaching implants, such as an annuloplasty ring as shown in e.g. FIGS. 9*a-b*, so that the ring can be securely attached, e.g. even if having different diameters of a first (700') and second ring (701, 701') on either side of the valve.

The distal portion 605, 605', may be arranged substantially perpendicular to the longitudinal direction 602 in the relaxed shape, i.e. extending substantially in the outward direction as illustrated in FIG. 7. This improves retention of the clip.

The distal portion 605, 605', may comprise a concave portion 608, being concave towards the bridging portion. This allows the clip to conform to a ring on the second side 901 of the valve as seen in FIGS. 8, 11*a*, for improved fixation. Also the concave shape will allow the tip 609 of the clip 600 to be directed upwards towards the second side 901, thereby minimizing the risk of the tip 609 penetrating any other tissue when moving with the beating heart. Thus the clip may be substantially W-shaped, where the distal portions 605, 605', form an angle against the outward direction 607 (FIG. 7) and in a direction towards the bridging portion 604.

The bridging portion 604 may be arranged to fixate an implant 700, 700', such as an annuloplasty ring to a first side 900 of a heart valve. The distal portion may thus comprise a tip portion 609 configured for penetrating into tissue, wherein in said relaxed shape, the tip portion is arranged to penetrate tissue on a second side 901 of the heart valve, opposite the first side 900.

The tip portion may be arranged to penetrate tissue from a direction substantially parallel to the longitudinal direction 602. The tip may also penetrate the tissue on the second side 901 in a specified angle relative the longitudinal direction 602. Retention force of the clip may in this way be optimized for various implants.

As further illustrated in FIG. 7, the tip portion 609 may be arranged to penetrate tissue at a first penetration site 610 on the first side 900 and arranged to penetrate tissue at a second penetration site 611 on the second side 901, where the second penetration site is displaced in the outward direction 607 from the first penetration site 610. This allows secure fixation of the clip and the amount of displacement can be various to suit various procedures and implants.

The bridge portion 604 may conform to the shape of an implant, such as the shape of a cross-section of an annuloplasty ring. By conforming to the shape of the implant the risk of dislodgement is reduced.

The distal portion 605, 605', may be arranged substantially parallel with the longitudinal direction in the delivery shape. This the delivery device 100, as described above, applies a restraining force on the clip so that the legs are kept substantially parallel and the distal portion can be delivered through the mentioned first penetration site 610, and then as the retention force from the stapling device 100, i.e. from the clip guides 105, 105, is removed when the clip 600 is pushed out of the stapling device, the clip 600 can assume the relaxed shape and the distal portions 605, 605', bend in the outward direction 607.

The clip may comprise a shape memory material, and the clip can thus be resiliently biased to move from the delivery shape to the relaxed shape when inserted into tissue.

The distal portion, in the relaxed shape, may have a shape that conforms to the shape of an implant, such as the shape of a cross-section of an annuloplasty ring 700, 700', such that the distal portion is arranged to fixate the implant to a second side of said heart valve, opposite said first side. This is illustrated in FIGS. 8 and 11*a*, where the distal portion is positioned around the implant also on the second side 901.

The distal portion, in the relaxed shape, may be arranged to exert a counter force in the longitudinal direction 602 against the bridging portion 604 so that the clip is adapted as a clamp, whereby the bridging portion is adapted to force an implant, such as an annuloplasty ring, against the first side 900.

Figure 12:
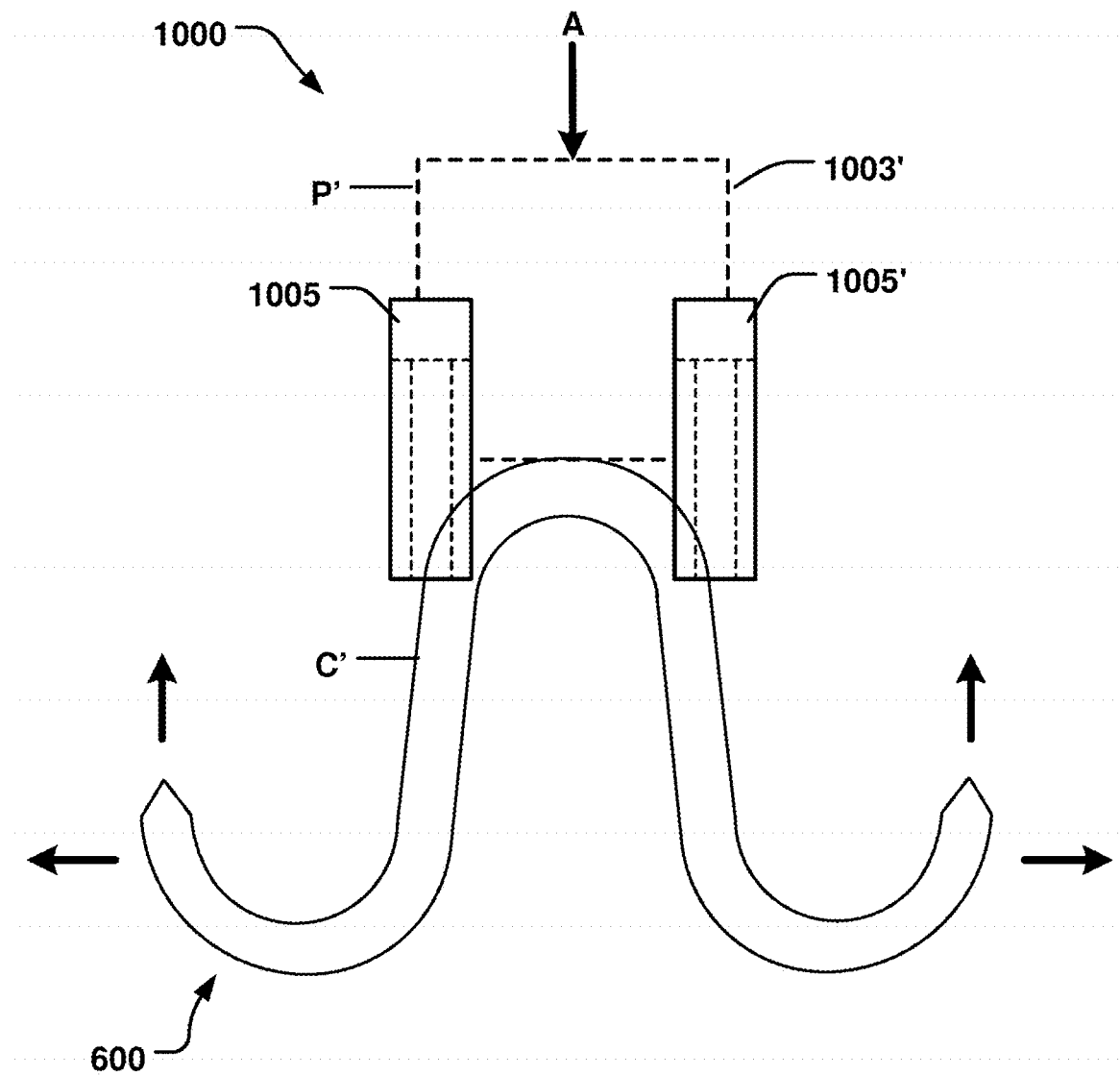
FIG. 12 is an illustration of a clip according to embodiments of the invention when being delivered from a stapling device.

The stapling device 100 described previously is adapted for attaching a clip 205, 600. FIG. 12 illustrates the stapling device 100 with pusher unit 103' pushing the clip 600 out from the clip guides 105, 105', as described above.

A stapling kit is thus also disclosed comprising a stapling device 100 and a clip 205, 600.

Figure 10:
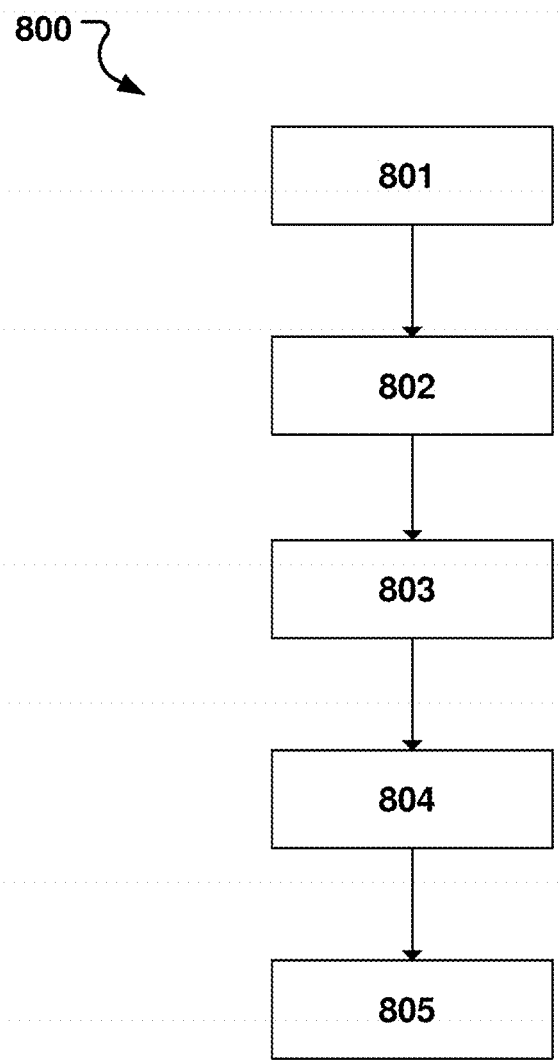
FIG. 10 is a flow chart illustrating a method according to embodiments of the invention.

FIG. 10 illustrates a method 800 of delivering a clip 600 to a target site comprising; positioning 801 a proximal portion 603, 603' of the clip over an annuloplasty ring at a first side 900 of a heart valve, positioning 803 a distal portion 605, 605' of the clip having a tip 609 on a second side of the heart valve, opposite said first side, so that the tip portion is arranged to penetrate tissue on the second side 901.

The method 800 may comprise penetrating 804 tissue on the second side with the tip from a direction substantially parallel to the longitudinal direction.

The method may comprise penetrating 802 tissue at a first penetration site 610 on the first side and penetrating 805 tissue at a second penetration site 611 on the second side, where the second penetration site is displaced in an outward direction 607 from the first penetration site.

FIG. 11 is an illustration of a stapling device 1000 for attaching a clip 2005, such as a clip 600 described above, to tissue comprising a sheath 1001 having a distal end 1002 for delivery of the clip, and a pusher unit 1003, 1003', being movable inside the sheath along a longitudinal direction 1004 of the sheath. The distal end comprises a clip guide 1005, 1005', in which the clip is movable in the longitudinal direction. The clip guide has a closed (G) configuration in which the clip guide is adapted to apply a restraining force on the clip so that the clip assumes a delivery shape (C). The pusher unit 1003, 1003', is movable from a proximal position (P) in which the clip guide is in the closed configuration, to a distal position (P') in which the pusher unit 1003, 1003', engages the clip guide 1005, 1005', and the clip guide is in the open configuration, see FIG. 12, where the clip is released.

By a single step movement, of the pusher 1003, 1003', from the proximal position (P) to the distal position (P') the clip 2005, 600, is transferred from the delivery shape to the relaxed shape. If the clip is inserted into the tissue in the delivery shape it can thus be conveniently and quickly transferred to towards the relaxed shape, in which it may clamp the tissue and fixate the position of e.g. an implant such an annuloplasty implant. The single step movement also provides for a simple and inexpensive device to manufacture, which also can be made as a single-use disposable device. The clip may be preloaded into the sheath 1001. Since the clip has its delivery shape already when the pusher 1003, 1003', is in the proximal position there is no additional action needed to engage the clip to transfer it into the delivery shape. This also allows for achieving improved stability in the longitudinal direction 1004 as explained below when the clip is in the delivery shape, and allowing for further guiding in the longitudinal direction 1004 when the pusher is engaged to the distal position.

Thus, by having a clip guide 1005, 1005', in which the clip is movable in the longitudinal direction 1004 of the sheath, while being transferred from the closed to the open configuration, the position of the clip in the longitudinal direction 1004 can be ensured to thereby attain high stability and accuracy when positioning of the clip in the delivery shape until the clip is fixated in the relaxed shape. In the proximal position of the pusher (FIG. 11), when the clip 205, 600, is restrained to assume its delivery shape, the clip can be positioned in the tissue due to the legs extending well outside the clip guide 1005, 1005. In this configuration, the clip guide holds the clip securely, since it functions as a guide in the longitudinal direction, so that the clip can be inserted into tissue without tilting or otherwise dislocate relative the longitudinal axis 104. As the pusher 1003' moves to the distal position (FIG. 12) the clip guides 1005, 1005', guides the clip 205, 600, in the longitudinal direction, maintaining a stable delivery path, while the clip assumes the relaxed shape, such as the W-formed shape illustrated in FIG. 12. The stable delivery path in the longitudinal direction 1004 make sure that there is no uncertainty in the position of the clip relative the sheath, crucial e.g. when operating in difficult conditions. The relaxed shape of the clip may be determined by heat treatment procedure, and the clip may be formed of a nitinol or another suitable material for heat-setting. The clip may not fully assume its relaxed shape when inserted into tissue due to the counter force exerted from the tissue on the clip, but the clip will strive to the relaxed shape which results in a compressive force between the clip and tissue.

The clip guide 1005, 1005', may comprise a clip track 1006, 1006', being arranged to partly enclose a leg 2000, 2000', 601, 601', of the clip 205, 600 and apply the restraining force previously mentioned and thereby align the clip in the longitudinal direction 1004 when the clip guide is in the closed configuration. Hence, when the clip is in the delivery shape, the clip track 1006, 1006', of the clip guide may force the leg, or legs of the clip into a certain position such as in the longitudinal direction 1004. The clip tracks 1006, 1006, may thus also be aligned in this direction. However, it is conceivable that the clip tracks 1006, 1006', may have an angle relative the longitudinal axis 1004 in certain applications in order to be able to deliver the clip in a certain angle relative the sheath. By having a clip track 1006, 1006', an improved alignment of the clip can be provided so that it follows a desired path when being transferred from the delivery shape in which the legs are restrained, to the relaxed shape.

The clip guide 1005, 1005', may comprise two guide parts 1007, 1008, 1007', 1008', being separable in opposite directions B, B' and in directions perpendicular to the longitudinal direction 1004. The separation of the two guide parts 1007, 1008, 1007', 1008', removes the restraining force on the clip so that the clip can assume its relaxed shape. This provides for particularly improved functionality for transferring the clip 2005, 600 from the delivery shape to the relaxed shape.

The pusher unit 1003 may comprise a distal tongue 1003' arranged to push the clip through the clip guide 1005, 1005', in the longitudinal direction 1004 and move the clip guide 1005, 1005', from the closed configuration to the open configuration. Hence, it provides for moving the clip along the longitudinal axis 1004 with the pusher and simultaneously moving the clip guide from the closed to the open configuration so that the clip can fixated in the relaxed shape C'.

The clip guide 1005, 1005', may comprise a first 1005 and a second 1005' clip guide arranged at radially opposite peripheries of the sheath 1001 and extending in the longitudinal direction 1004. This is illustrated in the exemplary embodiment of FIG. 11, and allows for improved accuracy in guiding the clip when moving the clip forward by ensuring guiding at both sides of the clip being positioned radially across the sheath 1001. Tilting or other dislocation of the clip is prevented.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An implant delivery system comprising an implant and a clip for fixing the implant to a tissue, wherein:
   said clip comprises a first leg having a proximal end and a distal end and a second leg having a proximal end and a distal end;
   a distal end of the clip forms a tapered shape adapted to pierce the tissue;
   the first leg and the second leg are joined at their distal ends at a point on the distal end of the clip;
   the first leg or the second leg comprises a proximal connecting element that releasably connects to a delivery device;
   the proximal ends of the first and second legs are spaced apart from each other by a first separation distance when the clip is in a delivery shape;
   the proximal ends of the first and second legs are spaced apart from each other by a second separation distance when the clip is compressed to an implanted shape;
   the second separation distance is shorter than said first separation distance; and
   the first leg or the second leg comprises a proximal engagement portion extending radially outwardly such that, when being drawn into a catheter, an edge portion of said catheter pushes the proximal engagement portion radially inwards.

2. The system according to claim 1, further comprising a delivery device comprising an angled surface that engages with the clip and applies a force to bend a proximal portion of the first leg or a proximal portion of the second leg when being drawn towards the angled surface.

3. The system according to claim 1, wherein:
   the implant is an annuloplasty implant,
   the tissue is heart valve tissue,
   the first leg and the second leg of the clip form an upwardly open receiving portion extending from the distal point of the clip and
   the receiving portion is configured to receive and fix the annuloplasty implant into position on a heart valve.

4. The system according to claim 3, wherein the annuloplasty implant is helix-shaped and comprises a first ring and a second ring and wherein the receiving portion is adapted to receive and fix said first and second rings on either side of the heart valve.

5. The system according to claim 4, where said receiving portion has a length corresponding to at least the sum of diameters of cross-sections of said first ring and said second ring of the helix-shaped implant, when positioned on either side of said heart valve.

6. The system according to claim 5, further comprising a fixation member being attachable to proximal ends of said first and second legs of said clip, and being adapted to fix said clip in said implanted shape, whereby said fixation member tensions said first and second legs against said annuloplasty implant.

7. An implant delivery system comprising an implant and a clip for fixing the implant to a tissue wherein:
   said clip comprises a first leg having a proximal end and a distal end and a second leg having a proximal end and a distal end;
   a distal end of the clip forms a tapered shape adapted to pierce the tissue;
   the first leg and the second leg are joined at their distal ends at a point on the distal end of the clip; and
   the first leg or the second leg comprises a proximal connecting element that releasably connects to a delivery device
   and wherein said system further comprises a catheter and a fixation member that attaches to proximal ends of the first leg and the second leg of the clip to fix the clip in an implanted shape.

8. The system according to claim 7, wherein the catheter comprises a sheath for attaching the fixation member to the clip and a connector wire that engages with and releasably connects to the proximal connecting element.

9. A system comprising a clip and an annuloplasty implant wherein:
   the clip comprises a first leg and a second leg, said first leg and said second leg being joined at respective distal ends at a distal point of the clip, said distal point forming a tapered shape of the clip being adapted to pierce tissue,
   said distal point and at least a portion of said legs form the tapered shape of the clip,
   said first leg or said second leg comprises a proximal connecting element for connecting to a delivery device, said first and second legs form an upward open receiving portion extending from said distal point, said receiving portion being adapted to receive and fix a position of the annuloplasty implant to a heart valve, and the first leg or the second leg comprises a proximal engagement portion extending radially outwardly such that, when being drawn into a catheter, an edge portion of said catheter pushes the proximal engagement portion radially inwards, the system further comprising a fixing member being attachable to proximal ends of said first leg and said second leg and being adapted to fix the clip in an implanted shape, whereby the fixing member tensions said first leg and said second leg against the annuloplasty implant.

10. The system of claim 9, wherein the annuloplasty implant comprises a helix-shaped implant having a first ring and a second ring and wherein said receiving portion is adapted to receive and fix said first ring and said second ring on opposite sides of a heart valve.

11. The system of claim 10, wherein said receiving portion has a length corresponding to at least a sum of diameters of cross-sections of said first and said second ring of the helix-shaped implant, when positioned on opposite sides of said heart valve.

12. The system of claim 9, wherein proximal ends of said first leg and said second leg are spaced apart in a delivery shape by a first distance and are compressible to the implanted shape in which said first leg and said second leg are spaced apart by a second distance that is shorter than said first distance.

13. The system of claim 12, wherein said clip comprises a proximal tapered portion adapted to pierce tissue, said proximal tapered portion being tapered in a direction opposite to a direction of taper of said tapered shape of said distal point.

14. The system of claim 12, wherein said clip is V-shaped.

15. The system of claim 12, wherein said first leg or said second leg comprises at least one reduced diameter portion, said reduced diameter portion being a predefined bending point at which said clip bends upon application of a force when, in use, said clip is being transformed from said delivery shape to said implanted shape.

16. The system of claim 12, further comprising said delivery device comprising a connector wire being releasably connectable to said proximal connecting element.

17. The system of claim 16, wherein:
said delivery device comprises said catheter;
said proximal engagement portion extends radially outwardly towards said catheter;
when in use, said proximal engagement portion is withdrawn into said catheter; and
an edge portion of said catheter pushes said proximal engagement portion radially inwards.

18. The system of claim 16, wherein said delivery device comprises a sheath for attaching said fixation fixing member to said clip, and the connector wire is engageable with the proximal connecting element for releasably connecting thereto.

19. The system of claim 16, wherein said delivery device comprises an angled surface that is engageable with said clip for applying a force to bend a proximal portion of said first leg or said second leg when, in use, being withdrawn towards said angled surface.

* * * * *